(12) United States Patent
Tilson et al.

(10) Patent No.: US 11,122,971 B2
(45) Date of Patent: Sep. 21, 2021

(54) DEVICE AND METHOD FOR ENHANCED VISUALIZATION OF THE SMALL INTESTINE

(71) Applicant: NEPTUNE MEDICAL INC., Burlingame, CA (US)

(72) Inventors: Alexander Q. Tilson, Burlingame, CA (US); Garrett J. Gomes, San Mateo, CA (US)

(73) Assignee: Neptune Medical Inc., Burlingame, CA (US)

( * ) Notice: Subject to any disclaimer, the term of this patent is extended or adjusted under 35 U.S.C. 154(b) by 90 days.

(21) Appl. No.: 16/325,497

(22) PCT Filed: Aug. 18, 2017

(86) PCT No.: PCT/US2017/047591
§ 371 (c)(1),
(2) Date: Feb. 14, 2019

(87) PCT Pub. No.: WO2018/035452
PCT Pub. Date: Feb. 22, 2018

(65) Prior Publication Data
US 2019/0223710 A1  Jul. 25, 2019

Related U.S. Application Data

(60) Provisional application No. 62/376,816, filed on Aug. 18, 2016.

(51) Int. Cl.
*A61B 1/00* (2006.01)
*A61B 1/32* (2006.01)
*A61B 1/04* (2006.01)

(52) U.S. Cl.
CPC ............ *A61B 1/32* (2013.01); *A61B 1/00085* (2013.01); *A61B 1/00101* (2013.01); *A61B 1/041* (2013.01)

(58) Field of Classification Search
None
See application file for complete search history.

(56) References Cited

U.S. PATENT DOCUMENTS

| 2,767,705 | A | 10/1956 | Moore |
| 3,859,986 | A | 1/1975 | Okada et al. |

(Continued)

FOREIGN PATENT DOCUMENTS

| AU | 2013207571 B1 | 8/2013 |
| CN | 2613655 Y | 4/2004 |

(Continued)

OTHER PUBLICATIONS

Tilson et al.; U.S. Appl. No. 16/631,473 entitled "Dynamically rigidizing overtube," filed Jan. 16, 2020.

(Continued)

*Primary Examiner* — Timothy J Neal
(74) *Attorney, Agent, or Firm* — Shay Glenn LLP

(57) ABSTRACT

A device for distending a body lumen for enhanced visualization with a capsule endoscope that includes a camera lens includes an attachment element configured to attach to the capsule endoscope and a plurality of struts extending from the attachment element and meeting at an apex. The plurality of struts are configured to extend both axially and radially away from the camera lens so as to form a frame therearound.

20 Claims, 14 Drawing Sheets

(56) References Cited

U.S. PATENT DOCUMENTS

| | | |
|---|---|---|
| 3,998,216 A | 12/1976 | Hosono |
| 4,066,071 A | 1/1978 | Nagel |
| 4,141,364 A | 2/1979 | Schultze |
| 4,176,662 A | 12/1979 | Frazer |
| 4,551,140 A | 11/1985 | Shinohara |
| 4,690,131 A | 9/1987 | Lyddy, Jr. et al. |
| 4,696,544 A | 9/1987 | Costella |
| 4,717,379 A | 1/1988 | Ekholmer |
| 4,794,412 A | 12/1988 | Casey et al. |
| 4,794,912 A | 1/1989 | Lia |
| 4,815,450 A | 3/1989 | Patel |
| 4,817,613 A | 4/1989 | Jaraczewski et al. |
| 4,893,613 A | 1/1990 | Hake |
| 4,959,058 A | 9/1990 | Michelson |
| 4,961,738 A | 10/1990 | Mackin |
| 5,018,436 A | 5/1991 | Evangelista et al. |
| 5,019,121 A | 5/1991 | Krauter |
| 5,037,386 A | 8/1991 | Marcus et al. |
| 5,105,819 A | 4/1992 | Wollschlager et al. |
| 5,123,421 A | 6/1992 | Sinofsky |
| 5,174,276 A | 12/1992 | Crockard |
| 5,188,595 A | 2/1993 | Jacobi |
| 5,251,611 A | 10/1993 | Zehel et al. |
| 5,337,733 A | 8/1994 | Bauerfeind et al. |
| 5,496,292 A | 3/1996 | Burnham |
| 5,531,685 A | 7/1996 | Hemmer et al. |
| 5,531,719 A | 7/1996 | Takahashi |
| 5,577,992 A | 11/1996 | Chiba et al. |
| 5,601,588 A | 2/1997 | Tonomura et al. |
| 5,607,435 A | 3/1997 | Sachdeva et al. |
| 5,632,734 A | 5/1997 | Galel et al. |
| 5,662,621 A | 9/1997 | Lafontaine |
| 5,746,692 A | 5/1998 | Bacich et al. |
| 5,759,151 A | 6/1998 | Sturges |
| 5,779,624 A | 7/1998 | Chang |
| 5,782,811 A | 7/1998 | Samson et al. |
| 5,882,347 A | 3/1999 | Mouris Laan et al. |
| 5,891,112 A | 4/1999 | Samson |
| 5,906,591 A | 5/1999 | Dario et al. |
| 5,916,145 A | 6/1999 | Chu et al. |
| 5,951,539 A | 9/1999 | Nita et al. |
| 5,976,074 A | 11/1999 | Moriyama |
| 6,159,187 A | 12/2000 | Park et al. |
| 6,162,171 A | 12/2000 | Ng et al. |
| 6,190,357 B1 | 2/2001 | Ferrari et al. |
| 6,309,346 B1 | 10/2001 | Farhadi |
| 6,364,878 B1 | 4/2002 | Hall |
| 6,468,203 B2 | 10/2002 | Belson |
| 6,485,409 B1 | 11/2002 | Voloshin et al. |
| 6,517,477 B1 | 2/2003 | Wendlandt |
| 6,547,724 B1 | 4/2003 | Soble et al. |
| 6,572,538 B2 | 6/2003 | Takase |
| 6,579,277 B1 | 6/2003 | Rabiner et al. |
| 6,610,007 B2 | 8/2003 | Belson et al. |
| 6,612,982 B1 | 9/2003 | Ouchi |
| 6,616,628 B2 | 9/2003 | Hayzelden |
| 6,620,126 B2 | 9/2003 | Unsworth et al. |
| 6,623,424 B2 | 9/2003 | Hayakawa et al. |
| 6,712,832 B2 | 3/2004 | Shah |
| 6,726,677 B1 * | 4/2004 | Flaherty .............. A61F 2/95 604/528 |
| 6,730,020 B2 | 5/2004 | Peng et al. |
| 6,780,151 B2 | 8/2004 | Grabover et al. |
| 6,783,491 B2 | 8/2004 | Saadat et al. |
| 6,790,173 B2 | 9/2004 | Saadat et al. |
| 6,793,621 B2 | 9/2004 | Butler et al. |
| 6,793,661 B2 | 9/2004 | Hamilton et al. |
| 6,800,056 B2 | 10/2004 | Tartaglia et al. |
| 6,869,393 B2 | 3/2005 | Butler |
| 6,899,673 B2 | 5/2005 | Ogura et al. |
| 6,911,004 B2 | 6/2005 | Kim et al. |
| 6,923,754 B2 | 8/2005 | Lubock |
| 6,960,162 B2 | 11/2005 | Saadat et al. |
| 6,974,411 B2 | 12/2005 | Belson |
| 6,984,203 B2 | 1/2006 | Tartaglia et al. |
| 7,060,199 B2 | 6/2006 | Woydt et al. |
| 7,172,552 B2 | 2/2007 | Wendlandt |
| 7,214,230 B2 | 5/2007 | Brock et al. |
| 7,288,101 B2 | 10/2007 | Deem et al. |
| 7,291,127 B2 | 11/2007 | Eidenschink |
| 7,365,509 B2 | 4/2008 | Park et al. |
| 7,438,712 B2 | 10/2008 | Chouinard |
| 7,511,733 B2 | 3/2009 | Takizawa et al. |
| 7,537,562 B2 | 5/2009 | Takano |
| 7,559,916 B2 | 7/2009 | Smith et al. |
| 7,591,782 B2 | 9/2009 | Fujikura |
| 7,598,652 B2 | 10/2009 | Kornbluh et al. |
| 7,695,428 B2 | 4/2010 | Machida |
| 7,736,323 B2 | 6/2010 | Von Weymarn-Scharli |
| 7,837,615 B2 | 11/2010 | Le et al. |
| 7,850,725 B2 | 12/2010 | Vardi et al. |
| 7,901,347 B2 | 3/2011 | Sekiguchi et al. |
| 7,909,755 B2 | 3/2011 | Itoi |
| 7,918,819 B2 | 4/2011 | Karmarkar et al. |
| 7,918,845 B2 | 4/2011 | Saadat et al. |
| 7,931,661 B2 | 4/2011 | Saadat et al. |
| 7,935,047 B2 | 5/2011 | Yoshida et al. |
| 7,947,000 B2 | 5/2011 | Vargas et al. |
| 7,957,790 B2 | 6/2011 | Kleen |
| 7,970,455 B2 | 6/2011 | Zilberstein et al. |
| 7,988,621 B2 | 8/2011 | Smith et al. |
| 8,047,236 B2 | 11/2011 | Perry |
| 8,075,476 B2 | 12/2011 | Vargas |
| 8,092,374 B2 | 1/2012 | Smith et al. |
| 8,109,953 B1 | 2/2012 | King, III et al. |
| 8,125,755 B2 | 2/2012 | Garcia et al. |
| 8,192,422 B2 | 6/2012 | Zubiate et al. |
| 8,206,287 B2 | 6/2012 | Matsuo |
| 8,226,548 B2 | 7/2012 | Kucklick |
| 8,241,299 B2 | 8/2012 | Hibner |
| 8,246,575 B2 | 8/2012 | Viola |
| 8,257,257 B2 | 9/2012 | Takizawa et al. |
| 8,298,161 B2 | 10/2012 | Vargas |
| 8,361,090 B2 | 1/2013 | Belson |
| 8,366,606 B2 | 2/2013 | Watanabe et al. |
| 8,388,519 B2 | 3/2013 | Garcia et al. |
| 8,439,825 B2 | 5/2013 | Sekiguchi |
| 8,460,179 B2 | 6/2013 | Ikeda et al. |
| 8,485,968 B2 | 7/2013 | Weimer et al. |
| 8,496,648 B2 | 7/2013 | Rogers |
| 8,506,479 B2 | 8/2013 | Piskun et al. |
| 8,517,923 B2 | 8/2013 | Belson et al. |
| 8,545,491 B2 | 10/2013 | Abboud et al. |
| 8,550,989 B2 | 10/2013 | Dohi et al. |
| 8,556,804 B2 | 10/2013 | Smith et al. |
| 8,663,096 B2 | 3/2014 | Viola |
| 8,663,196 B2 | 3/2014 | Kassab et al. |
| 8,708,894 B2 | 4/2014 | Smith et al. |
| 8,721,530 B2 | 5/2014 | Ohline et al. |
| 8,753,312 B2 | 6/2014 | Bowe et al. |
| 8,920,369 B2 | 12/2014 | Salahieh et al. |
| 8,969,639 B2 | 3/2015 | Xu et al. |
| 9,011,318 B2 | 4/2015 | Choset et al. |
| 9,066,655 B2 | 6/2015 | Stefanchik et al. |
| 9,125,653 B2 | 9/2015 | Kovach |
| 9,155,451 B2 | 10/2015 | Smith et al. |
| 9,192,284 B2 | 11/2015 | Hirsch et al. |
| 9,192,288 B2 | 11/2015 | Okaniwa |
| 9,211,140 B2 | 12/2015 | Lauryssen et al. |
| 9,220,398 B2 | 12/2015 | Woodley et al. |
| 9,226,825 B2 | 1/2016 | Starksen et al. |
| 9,241,611 B2 | 1/2016 | Konno |
| 9,254,123 B2 | 2/2016 | Alvarez et al. |
| 9,295,511 B2 | 3/2016 | Smith et al. |
| 9,358,073 B2 | 6/2016 | Piligian et al. |
| 9,364,955 B2 | 6/2016 | Oyola et al. |
| 9,386,910 B2 | 7/2016 | West |
| 9,498,108 B1 | 11/2016 | Lombardi |
| 9,498,198 B2 | 11/2016 | Kim et al. |
| 9,505,125 B2 | 11/2016 | Zubiate et al. |
| 9,585,546 B2 | 3/2017 | Surti et al. |
| 9,610,068 B2 | 4/2017 | Kappel et al. |
| 9,763,562 B2 | 9/2017 | Avitsian et al. |
| 9,814,372 B2 | 11/2017 | Smith et al. |

(56) References Cited

U.S. PATENT DOCUMENTS

| | | |
|---|---|---|
| 9,913,570 B2 | 3/2018 | Kucharski et al. |
| 9,937,324 B2 | 4/2018 | Kim et al. |
| 10,092,291 B2 | 10/2018 | Voegele et al. |
| 10,307,042 B2 | 6/2019 | Lombardi |
| 10,463,495 B2 | 11/2019 | Rogers et al. |
| 2002/0107478 A1 | 8/2002 | Wendlandt |
| 2003/0023259 A1 | 1/2003 | Dubrul et al. |
| 2003/0083546 A1 | 5/2003 | Butler et al. |
| 2003/0153866 A1 | 8/2003 | Long et al. |
| 2003/0208220 A1 | 11/2003 | Worley et al. |
| 2003/0216622 A1* | 11/2003 | Meron .................. A61B 5/686 600/300 |
| 2003/0216691 A1 | 11/2003 | Jacobson |
| 2004/0019252 A1 | 1/2004 | Hirata |
| 2004/0044350 A1 | 3/2004 | Martin et al. |
| 2004/0092960 A1 | 5/2004 | Abrams et al. |
| 2004/0186349 A1* | 9/2004 | Ewers ................ A61B 1/00082 600/114 |
| 2004/0243227 A1 | 12/2004 | Starksen et al. |
| 2004/0260236 A1 | 12/2004 | Manning et al. |
| 2005/0085829 A1 | 4/2005 | Kraemer et al. |
| 2005/0165275 A1 | 7/2005 | Von Felten et al. |
| 2005/0203340 A1 | 9/2005 | Butler et al. |
| 2005/0272974 A1 | 12/2005 | Iddan |
| 2005/0277966 A1* | 12/2005 | Ewers ................ A61B 17/0401 606/153 |
| 2006/0041188 A1 | 2/2006 | Dirusso et al. |
| 2006/0047183 A1 | 3/2006 | Park |
| 2006/0058582 A1 | 3/2006 | Maahs et al. |
| 2006/0129130 A1 | 6/2006 | Tal et al. |
| 2006/0192465 A1 | 8/2006 | Kornbluh et al. |
| 2006/0258906 A1 | 11/2006 | Binmoeller |
| 2006/0264707 A1 | 11/2006 | Kinney |
| 2006/0287666 A1 | 12/2006 | Saadat et al. |
| 2007/0015965 A1 | 1/2007 | Cox et al. |
| 2007/0038025 A1 | 2/2007 | Yoshida |
| 2007/0088367 A1 | 4/2007 | Von Weymarn-Scharli |
| 2007/0100414 A1 | 5/2007 | Licata et al. |
| 2007/0106302 A1 | 5/2007 | Ortiz |
| 2007/0118015 A1 | 5/2007 | Wendlandt |
| 2007/0161851 A1* | 7/2007 | Takizawa .................. A61B 1/31 600/102 |
| 2007/0219411 A1 | 9/2007 | Dejima et al. |
| 2007/0260121 A1 | 11/2007 | Bakos |
| 2008/0051635 A1* | 2/2008 | Tanaka ..................... A61B 1/06 600/160 |
| 2008/0058722 A1 | 3/2008 | Oepen et al. |
| 2008/0091073 A1 | 4/2008 | Park |
| 2008/0103440 A1 | 5/2008 | Ferren et al. |
| 2008/0139887 A1 | 6/2008 | Fitzpatrick |
| 2008/0172037 A1 | 7/2008 | Huang et al. |
| 2008/0188928 A1 | 8/2008 | Saiehieh et al. |
| 2008/0200762 A1 | 8/2008 | Stokes et al. |
| 2008/0214893 A1 | 9/2008 | Tartaglia et al. |
| 2008/0234546 A1* | 9/2008 | Kawano ............. A61B 1/00089 600/104 |
| 2008/0242928 A1 | 10/2008 | Kawano et al. |
| 2008/0262300 A1 | 10/2008 | Ewers et al. |
| 2008/0275299 A1 | 11/2008 | Park |
| 2009/0048483 A1 | 2/2009 | Yamamoto |
| 2009/0062611 A1 | 3/2009 | Toyama |
| 2009/0062837 A1 | 3/2009 | Gasche et al. |
| 2009/0112063 A1 | 4/2009 | Bakos et al. |
| 2009/0131752 A1 | 5/2009 | Park |
| 2009/0157068 A1 | 6/2009 | Kallel et al. |
| 2009/0187163 A1 | 7/2009 | Uihlein |
| 2009/0240202 A1 | 9/2009 | Drasler et al. |
| 2009/0264704 A1 | 10/2009 | Shtul |
| 2010/0010308 A1 | 1/2010 | Braun et al. |
| 2010/0016663 A1 | 1/2010 | Maisch et al. |
| 2010/0069712 A1 | 3/2010 | Yamaya |
| 2010/0076451 A1 | 3/2010 | Zwolinski et al. |
| 2010/0087711 A1 | 4/2010 | Edwards |
| 2010/0137686 A1 | 6/2010 | Meron et al. |
| 2010/0145151 A1 | 6/2010 | Fukunaga et al. |
| 2010/0160735 A1 | 6/2010 | Bakos |
| 2010/0204546 A1 | 8/2010 | Hassidov et al. |
| 2010/0268025 A1 | 10/2010 | Belson |
| 2010/0331625 A1 | 12/2010 | Rosemurgy et al. |
| 2010/0331820 A1 | 12/2010 | Prisco et al. |
| 2011/0015729 A1 | 1/2011 | Jimenez et al. |
| 2011/0040282 A1 | 2/2011 | Uihlein |
| 2011/0046442 A1 | 2/2011 | Matsushita |
| 2011/0049282 A1 | 3/2011 | Danielsson |
| 2011/0054253 A1 | 3/2011 | Jordá Albiñana et al. |
| 2011/0237888 A1 | 9/2011 | Matsushita |
| 2011/0245611 A1 | 10/2011 | Yeh et al. |
| 2011/0282149 A1 | 11/2011 | Vargas et al. |
| 2011/0306950 A1 | 12/2011 | Cucin |
| 2012/0022329 A1 | 1/2012 | Wagh et al. |
| 2012/0041291 A1 | 2/2012 | Ferren et al. |
| 2012/0108902 A1 | 5/2012 | Frassica et al. |
| 2012/0130173 A1 | 5/2012 | Lutze et al. |
| 2012/0143005 A1 | 6/2012 | Yeh et al. |
| 2012/0165607 A1 | 6/2012 | Ashida et al. |
| 2012/0165792 A1 | 6/2012 | Ortiz et al. |
| 2012/0172651 A1 | 7/2012 | Cutrer |
| 2012/0209062 A1 | 8/2012 | Qiao |
| 2012/0277528 A1 | 11/2012 | Qiao |
| 2013/0131641 A1 | 5/2013 | Jimenez et al. |
| 2013/0190565 A1 | 7/2013 | Gora et al. |
| 2013/0338440 A1 | 12/2013 | Sinai et al. |
| 2014/0005683 A1 | 1/2014 | Stand et al. |
| 2014/0081169 A1 | 3/2014 | Gerding et al. |
| 2014/0088459 A1 | 3/2014 | Roush et al. |
| 2014/0142393 A1 | 5/2014 | Piskun et al. |
| 2014/0155702 A1 | 6/2014 | Tilson et al. |
| 2014/0155783 A1 | 6/2014 | Starksen et al. |
| 2014/0188054 A1 | 7/2014 | Iijima et al. |
| 2014/0243873 A1* | 8/2014 | Franklin ........... A61M 25/0097 606/194 |
| 2014/0275860 A1* | 9/2014 | Rottenberg .............. A61B 1/06 600/302 |
| 2014/0276642 A1 | 9/2014 | Cully et al. |
| 2014/0371764 A1 | 12/2014 | Oyola et al. |
| 2015/0073409 A1 | 3/2015 | Watson et al. |
| 2015/0094656 A1 | 4/2015 | Salahieh et al. |
| 2015/0133729 A1 | 5/2015 | Reydel |
| 2015/0148602 A1 | 5/2015 | Hill et al. |
| 2015/0148606 A1 | 5/2015 | Rottenberg et al. |
| 2015/0164314 A1 | 6/2015 | Peterson |
| 2015/0216589 A1 | 8/2015 | Wittenberger et al. |
| 2015/0342608 A1 | 12/2015 | Hernandez |
| 2016/0007832 A1 | 1/2016 | Shimada |
| 2016/0066773 A1 | 3/2016 | Cooper et al. |
| 2016/0096004 A1 | 4/2016 | Gerrans et al. |
| 2016/0129547 A1 | 5/2016 | Duescher et al. |
| 2016/0136393 A1 | 5/2016 | Tsai et al. |
| 2016/0174829 A1 | 6/2016 | Reydel |
| 2016/0198935 A1 | 7/2016 | Choi et al. |
| 2016/0270870 A1 | 9/2016 | Kowshik |
| 2016/0287059 A1 | 10/2016 | Ha et al. |
| 2016/0324412 A1 | 11/2016 | Hassidov et al. |
| 2017/0156567 A1 | 6/2017 | Kaneko |
| 2017/0157363 A1 | 6/2017 | Barrish et al. |
| 2018/0015257 A1 | 1/2018 | Krolik et al. |
| 2018/0184885 A1 | 7/2018 | St. George |
| 2018/0249893 A1 | 9/2018 | Yeung et al. |
| 2018/0263469 A1 | 9/2018 | Okaniwa et al. |
| 2018/0271354 A1 | 9/2018 | Tilson et al. |
| 2018/0289925 A1 | 10/2018 | Palmer et al. |
| 2018/0361116 A1 | 12/2018 | Quick et al. |

FOREIGN PATENT DOCUMENTS

| | | |
|---|---|---|
| CN | 101129255 A | 2/2008 |
| CN | 201899767 U | 7/2011 |
| CN | 104287684 B | 3/2016 |
| EP | 401129 A1 | 12/1990 |
| EP | 1662972 A2 | 6/2006 |
| EP | 1695657 A1 | 8/2006 |
| EP | 1487318 B1 | 3/2008 |
| EP | 2016914 A2 | 1/2009 |

(56) References Cited

FOREIGN PATENT DOCUMENTS

| | | |
|---|---|---|
| EP | 1499227 B1 | 10/2010 |
| EP | 2364637 A1 | 9/2011 |
| EP | 2368481 A1 | 9/2011 |
| EP | 2368483 A1 | 9/2011 |
| EP | 3256052 A1 | 12/2017 |
| JP | H05293077 A | 11/1993 |
| JP | 2002125921 A | 5/2002 |
| JP | 2005152300 A | 6/2005 |
| JP | 03965108 B2 | 8/2007 |
| KR | 10-2015-0131502 A | 11/2015 |
| WO | WO97/43941 A1 | 11/1997 |
| WO | WO99/053827 A1 | 10/1999 |
| WO | WO03/013348 A1 | 2/2003 |
| WO | WO2007/035931 A2 | 3/2007 |
| WO | WO2008/041809 A1 | 4/2008 |
| WO | WO2008/122997 A1 | 10/2008 |
| WO | WO2011/018147 A1 | 2/2011 |
| WO | WO2011/018157 A1 | 2/2011 |
| WO | WO2011/148172 A2 | 12/2011 |
| WO | WO2012/054480 A2 | 4/2012 |
| WO | WO2012/080947 A1 | 6/2012 |
| WO | WO2017/041052 A1 | 3/2017 |
| WO | WO2018/035452 A1 | 8/2017 |
| WO | WO2019/018682 A1 | 1/2019 |

OTHER PUBLICATIONS

Entrada® colonic overtube product brochure downloaded from internet http://www.usendoscopy.com/~/media/Files/Documents/Spec-Sheet-International/760358c_entrada_intl_ss_web.pdf Accessed Date: Jun. 5, 2017 (year of pub sufficiently earlier than effective US filing date and any foreign priority date) 2009.

Filip et al.; Design, Implementation, and Testing of a miniature self-stabilizing capsule endoscope with wireless image transmission capabilities; Intl. Journal "Information Technologies & Knowledge"; 5(1); downloaded from http://www.foibg.com/ijitk/ijilk-vol05/ijitk05-1-p01.pdf on Jul. 28, 2016; (year of pub sufficiently earlier than effective US filing date and any foreign priority date) 2011.

Loeve et al.; Endoscope Shaft-Rigidity Control Mechanism: "Forguide"; IEEE Trans. on Biomed. Eng.; 59(2); pp. 542-551; Feb. 2012.

Shah et al.; Magnetic Imaging of Colonoscopy: An Audit of Looping, Accuracy and Ancillary maneuvers; Gastrointest. Endosc.; 52(1); pp. 1-8; Jul. 1, 2000.

Simi et al.; Design, Fabrication, and Testing of a Capsule With Hybrid Locomotion for Gastrointestinal Tract Exploration; IEEE/ASME Trans on Mechatronics; 15(2); pp. 170-x; Apr. 2010.

Valdastri et al.; Advanced Technologies for Gastrointestinal Endoscopy; Annu. Rev. Biomed. Eng.; 14; pp. 397-429; May 2012.

Zhao et al.; Development of a variable stiffness over tube based on low-melting-point-alloy for endoscopic surgery; J. Med. Devices; 10(2); 8 pages; May 12, 2016.

Loeve et al.; Vacuum packed particles as flexible endoscope guides with controllable rigidity; Granular Matter; 12(6); pp. 543-554; Jun. 24, 2010.

Tilson et al.; U.S. Appl. No. 17/057,240 entitled "Device and method for enhanced visualization of the small intestine," filed Nov. 20, 2020.

Tilson et al.; U.S. Appl. No. 17/152,706 entitled "Dynamically rigidizing composite medical structures," filed Jan. 19, 2021.

* cited by examiner

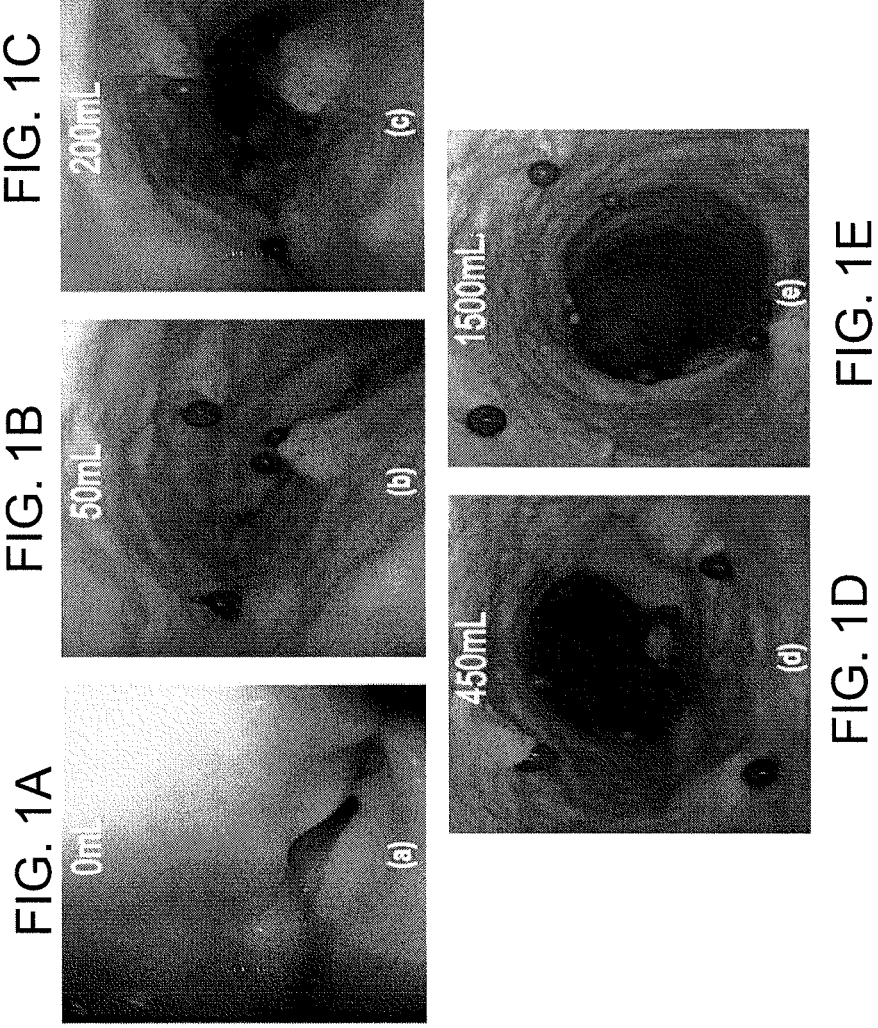

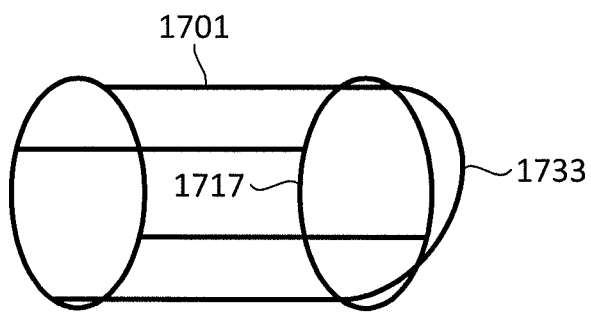
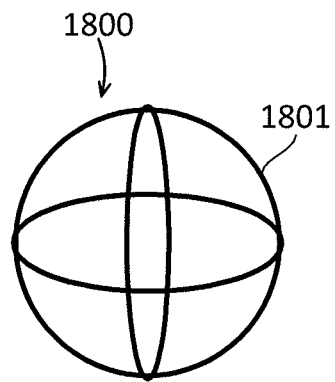
FIG. 17
FIG. 18
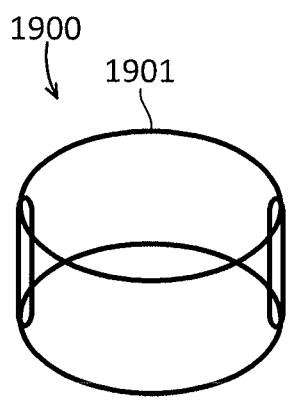
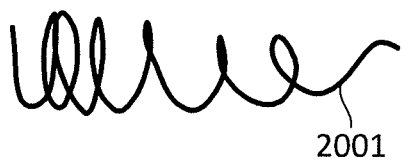
FIG. 19
FIG. 20

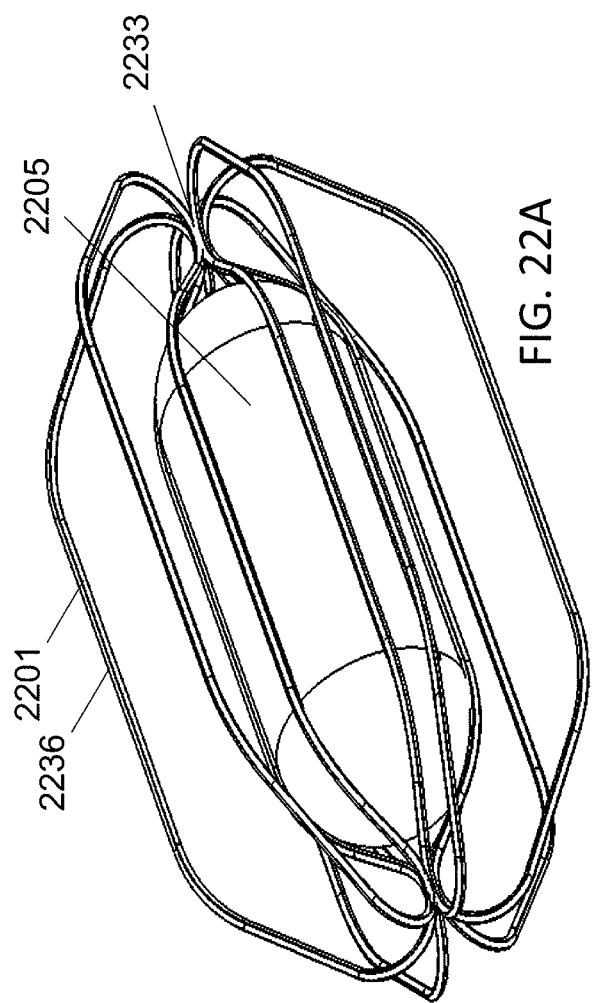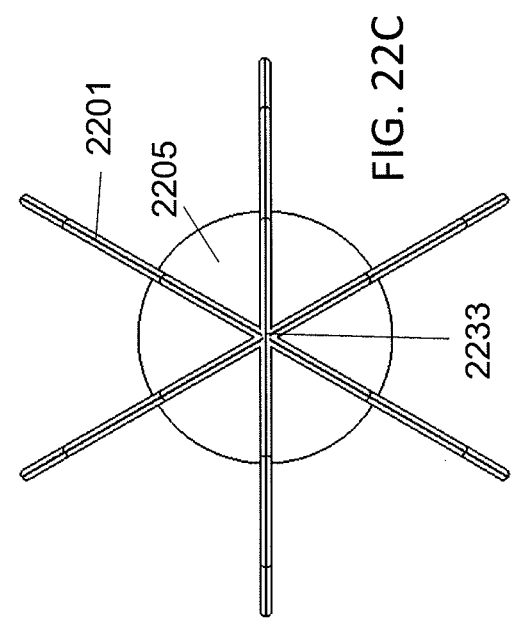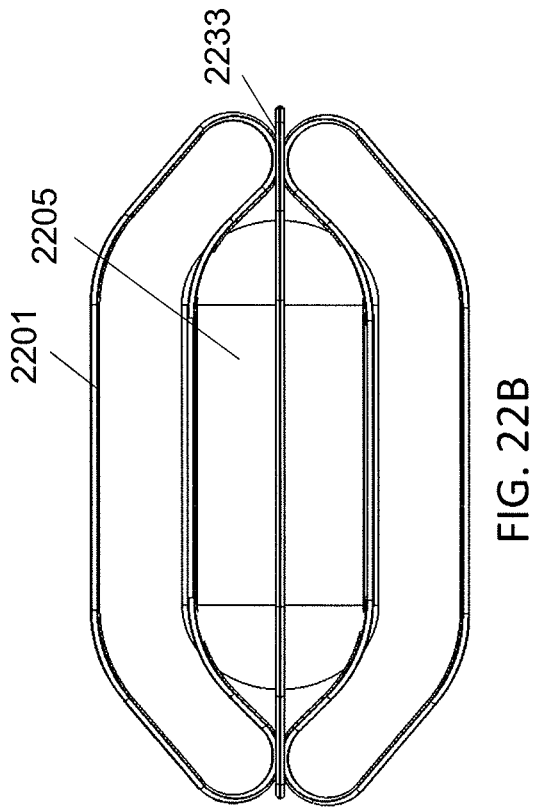

DEVICE AND METHOD FOR ENHANCED VISUALIZATION OF THE SMALL INTESTINE

CROSS REFERENCE TO RELATED APPLICATIONS

This application claims priority to U.S. Provisional Patent Application No. 62/376,816, filed Aug. 18, 2016 and titled "DEVICE AND METHOD FOR ENHANCED VISUALIZATION OF THE SMALL INTESTINE," the entirety of which is incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Endoscopy, the study or examination of the inside of the body, is a common procedure performed by gastroenterologists inside of the gastrointestinal (GI) tract. It is typically accomplished with long, slender endoscopes, either rigid or flexible.

For typical endoscopy, visualization of the GI tract is significantly enhanced by insufflation, i.e., the release of pressurized gas (air or CO2). Because collapsed tissue inhibits visualization, insufflation is used to expand or distend the GI tract so that it can be fully visualized. Without such inflation, endoscopy moves through only a portion of an often-flattened lumen, failing to image significant parts of the lumen. As a result, incomplete evaluation of the bowel is common when insufflation is not used. Luminal distention is therefore often critical for endoscopy for better visualization, detection, and the efficacy of the entire examination. FIGS. 1A-1E shows the advantages of insufflation distention during a typical endoscopy procedure. FIG. 1A shows the intestine in its deflated state with no markers visible. FIG. 1B shows that with just 50 mL of insufflation, 4 of the 9 markes become visible. FIG. 1C shows insufflation at 200 mL. FIG. 1D shows insufflation at 450 mL. FIG. 1E shows the intestine fully inflated at 1500 mL.

However, traditional endoscopy is invasive, usually requires anesthesia, and can be very difficult to move through the small intestine. Recently, there has been commercial success for a distinctly new class of devices known as capsule endoscopes (CE) (including pill cameras, pillcams, wireless capsule endoscopes, or video capsule endoscopes (VCE)). Capsule endoscopies have been revolutionary for gastroenterology, enabling diagnostic procedures that are non-invasive, do not require anesthesia, and provide visualization of anatomies that were previously poorly interrogated, including the small intestine. With capsule endoscopy, manufacturers have gone to great lengths to improve visualization, adding ever-more cameras, side-view cameras, rotating cameras, cameras with a widening field of view, or finer resolution, an increased quantity of more powerful LEDs, faster data transfer rates, and radically higher frame rates. However, none of these improvements are meaningful or helpful if the lumen is flattened and/or covers the lens.

For capsule endoscopy, luminal expansion techniques are currently not available. As such, the procedure's visualization, and thus its entire diagnostic yield and efficacy, is significantly limited. FIGS. 2A-2D show exemplary instances in which the field of view with a capsule endoscope can be obscured. FIG. 2A, for example, shows the lumen 200 collapsed around the capsule endoscope 222. FIG. 2B shows scope 222 oriented towards a fold in the wall of the lumen 200. FIG. 2C shows localized immersive mucosal contact of the lumen 220 with the scope 222. Finally, FIG. 2D shows deep folds in the lumen 200, which can hinder visualization with the scope 222. These exemplary scenarios can result in occlusion of the lens, a view of only the closed tissue, and/or an impartial view caused by blood, debris, or tissue interfering with the lens. As a result, typical capsule endoscope diagnostic efficacy rates are subpar, estimated at only around 50%. Despite patient experience advantages relative to traditional endoscopic devices, these suboptimal rates have prevented the devices from reaching their potential.

Studies have been performed with capsule endoscopes that release gas into the gastrointestinal tract for insufflation, and the results show radically improved visualization. Gas release in such studies was accomplished, for example, through the release of pressurized air or as the by-product of a chemical reaction. However, storing and methodically releasing pressurized air aboard a capsule in the gastrointestinal tract is problematic. Excessive localized gas release can cause patient discomfort. Chemical reactions struggle with heat, biocompatibility, foaming and bubbles, longevity, and adequate volume.

Capsule endoscopes including built-in radial extensions have been proposed as a means of making the device more lumen-centric to improve imaging, but these structures do not serve to adequately tent small intestine tissue, as the small intestine tissue is very thin, soft, and compliant and tends to fold over onto the lens of the scope.

A device for use with a capsule endoscope that addresses some or all of these problems is thus desired.

SUMMARY OF THE DISCLOSURE

In general, in one embodiment, a device for distending a body lumen for enhanced visualization with a capsule endoscope that includes a camera lens includes an attachment element configured to attach to the capsule endoscope and a plurality of struts extending from the attachment element and meeting at an apex. The plurality of struts are configured to extend both axially and radially away from the camera lens so as to form a frame therearound with the apex positioned a set axial distance away from the camera lens.

This and other embodiments can include one or more of the following features. The attachment element can be an annular ring. The attachment element can be configured to attach to the capsule endoscope through friction fit, adhesive, or clamping. The frame can include a shoulder that is positioned a maximum radial distance away from the capsule scope. The shoulder can be axially offset away from the camera lens. A distance between the shoulder and the apex can be between 10 mm and 30 mm. A diameter of the frame at the shoulder can be between 20 mm and 40 mm. The frame can include a tapered tip. An angle of the taper can be between 30° and 60°. The set axial distance can be between 25 mm and 45 mm. The struts of the plurality of struts can be separated by 30° to 120°. There can be between 4 and 6 struts in the plurality of struts. Each of the plurality of struts can be self-expandable. Each of the plurality of struts can be formed of a shape memory material. The frame can include a biodegradable portion.

In general, in one embodiment, a device for visualization of a body lumen includes a capsule endoscope with a camera lens and a plurality of struts extending from the capsule endoscope and meeting at an apex. The plurality of struts extend both axially and radially away from the camera lens so as to form a frame therearound with the apex positioned a set axial distance away from the camera lens.

This and other embodiments can include one or more of the following features. The frame can include a shoulder that is positioned a maximum radial distance away from the capsule endoscope. The shoulder can be axially offset away from the camera lens. A distance between the shoulder and the apex can be between 10 mm and 30 mm. A diameter of the frame at the shoulder can be between 20 mm and 40 mm. The frame can include a tapered tip. An angle of the taper can be between 30° and 60°. The set axial distance can be between 25 mm and 45 mm. The struts of the plurality of struts can be separated by 30° to 120°. There can be between 4 and 6 struts in the plurality of struts. Each of the plurality of struts can be self-expandable. Each of the plurality of struts can be formed of a shape memory material. The frame can include a biodegradable portion.

In general, in one embodiment, a method of enhancing visualization of a body lumen includes: (1) positioning a device including a capsule endoscope and a plurality of struts attached thereto into a body lumen; (2) expanding the plurality of struts of the device within the body lumen such that the plurality of struts extend both radially and axially away from a camera lens of the capsule endoscope and meet at an apex that is positioned a set axial distance away from the camera lens; and (3) imaging with the camera lens into the body lumen.

This and other embodiments can include one or more of the following features. The plurality of struts can form a frame around the camera lens upon expansion. The frame can include a shoulder that is positioned a maximum radial distance away from the capsule endoscope. The shoulder can be axially offset away from the camera lens. A distance between the shoulder and the apex can be between 10 mm and 30 mm. A diameter of the frame at the shoulder can be between 20 mm and 40 mm. The plurality of struts can form a frame around the camera lens upon expansion. The frame can include a tapered tip. An angle of the taper can be between 30° and 60°. The set axial distance can be between 25 mm and 45 mm. The struts of the plurality of struts can be separated by 30° to 120° upon expansion. There can be between 4 and 6 struts in the plurality of struts. Expanding the plurality of struts can include self-expanding the plurality of struts. Each of the plurality of struts can be formed of a shape memory material. The plurality of struts can form a frame around the camera lens upon expansion. The method can further include dissolving at least a portion of the frame to allow passage of the device from the body.

In general, in one embodiment, a device for distending a body lumen for enhanced visualization with a capsule endoscope that includes a camera lens includes an attachment element configured to attach to the capsule endoscope and a plurality of struts fixed to the attachment element. The plurality of struts are configured to self-expand from a constrained configuration to an expanded configuration in which the plurality of struts extend both axially and radially away from the camera lens so as to form a frame therearound.

This and other embodiments can include one or more of the following features. The struts can be configured to self-expand based upon a trigger within the body lumen. The attachment element can be an annular ring. The attachment element can be configured to attach to the capsule endoscope through friction fit, adhesive, or clamping. The frame can include a tapered tip. An angle of the taper can be between 30° and 60°. The struts of the plurality of struts can be separated by 30° to 120° in the expanded configuration. There can be between 4 and 6 struts in the plurality of struts. Each of the plurality of struts can be formed of a shape memory material. The frame can include a biodegradable portion.

In general, in one embodiment, a device for visualization of a body lumen includes a capsule endoscope with a camera lens and a plurality of struts attached to the capsule endoscope. The plurality of struts are configured to self-expand from a constrained configuration to an expanded configuration in which the plurality of struts extend both axially and radially away from the camera lens so as to form a frame therearound.

This and other embodiments can include one or more of the following features. The device can further include a covering around the struts configured to hold the plurality of struts in the constrained configuration. The covering can be configured to dissolve in the body lumen. The struts can be configured to self-expand based upon a trigger within the body lumen. The frame can include a tapered tip. An angle of the taper can be between 30° and 60°. The struts of the plurality of struts can be separated by 30° to 120° in the expanded configuration. There can be between 4 and 6 struts in the plurality of struts. Each of the plurality of struts can be formed of a shape memory material. The frame can include a biodegradable portion.

In general, in one embodiment, a method of enhancing visualization of a body lumen includes: (1) positioning a device including a capsule endoscope and a plurality of struts attached thereto into a body lumen; (2) self-expanding the plurality of struts of the device within the body lumen from a constrained configuration to an expanded configuration in which the plurality of struts extend both radially and axially away from a camera lens of the capsule endoscope; and (3) imaging with the camera lens through the frame into the body lumen.

This and other embodiments can include one or more of the following features. The frame can include a tapered tip. An angle of the taper can be between 30° and 60°. The struts of the plurality of struts can be separated by 30° to 120° in the expanded configuration. There can be between 4 and 6 struts in the plurality of struts. Each of the plurality of struts can be formed of a shape memory material. The plurality of struts can form a frame around the camera lens in the expanded configuration. The method can further include dissolving at least a portion of the frame to allow passage of the device from the body.

In general, in one embodiment, a device for distending a body lumen for enhanced visualization with a capsule endoscope that includes a camera lens includes an attachment element configured to attach to the capsule endoscope and a plurality of struts fixed to the attachment element. The plurality of struts are configured to extend both axially and radially away from the camera lens so as to form a frame therearound. The frame further includes one or more biodegradable portions.

This and other embodiments can include one or more of the following features. The one or more biodegradable portions can include a node between struts. The plurality of struts can include rounded ends upon biodegradation of the node. The one or more biodegradable portions can include a node within a strut. The frame can include a tapered tip. An angle of the taper can be between 30° and 60°. The struts of the plurality of struts can be separated by 30° to 120°. There can be between 4 and 6 struts in the plurality of struts. Each of the plurality of struts can be self-expandable. Each of the plurality of struts can be formed of a shape memory material. The attachment element can be an annular ring. The attachment element can be configured to attach to the capsule endoscope through friction fit, adhesive, or clamping.

In general, in one embodiment, a device for visualization of a body lumen includes a capsule endoscope with a camera lens and a plurality of struts attached to the capsule endoscope. The plurality of struts are configured to extend both axially and radially away from the camera lens so as to form a frame therearound. The frame further includes one or more biodegradable portions.

This and other embodiments can include one or more of the following features. The one or more biodegradable portions can include a node between struts. Each of the plurality of struts can include rounded ends upon biodegradation of the node. The one or more biodegradable portions can include a node within a strut. The frame can include a tapered tip. An angle of the taper can be between 30° and 60°. The struts of the plurality of struts can be separated by 30° to 120°. There can be between 4 and 6 struts in the plurality of struts. Each of the plurality of struts can be self-expandable. Each of the plurality of struts can be formed of a shape memory material.

In general, in one embodiment, a method of enhancing visualization of a body lumen includes (1) positioning a device including a capsule endoscope and a plurality of struts attached thereto into a body lumen; (2) expanding the plurality of struts of the device within the body lumen such that the plurality of struts extend both radially and axially away from a camera lens of the capsule endoscope to form a frame therearound; (3) imaging with the camera lens through the frame into the body lumen; and (4) dissolving at least a portion of the frame to allow passage of the device from the body lumen.

This and other embodiments can include one or more of the following features. The frame can include a tapered tip. An angle of the taper can be between 30° and 60°. The struts of the plurality of struts can be separated by 30° to 120° upon expansion. There can be between 4 and 6 struts in the plurality of struts. Each of the plurality of struts can be formed of a shape memory material. The method can further include dissolving at least a portion of the frame to allow passage of the device from the body. The portion of the frame can include a node between struts. The plurality of struts can include rounded ends upon biodegradation of the node. The portion of the frame can include a node within a strut.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1E show the intestine at various stages of insufflation.

FIG. 17 shows a luminal expansion device including a cylindrical cage with a tapered tip.

FIG. 18 shows a spherical luminal expansion device.

FIG. 19 shows a disk shaped luminal expansion device.

FIG. 20 shows a spiral luminal expansion device.

FIGS. 22A-C show an exemplary luminal expansion device for a side-viewing capsule endoscope.

DETAILED DESCRIPTION

Described herein are devices for use with a capsule endoscope (CE) (a pill camera, pillcam, wireless capsule endoscope, or video capsule endoscope (VCE)) that significantly aid in more complete luminal visualization during capsule endoscopy. The devices create local distension of gastrointestinal luminal tissue away from the camera, improving diagnostic yield.

Figure 2A:
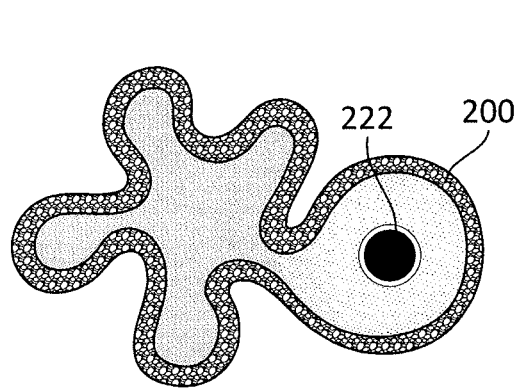
FIGS. 2A-2D are schematics showing exemplary instances in which the field of view with a capsule endoscope can be obscured.
Figure 2B:
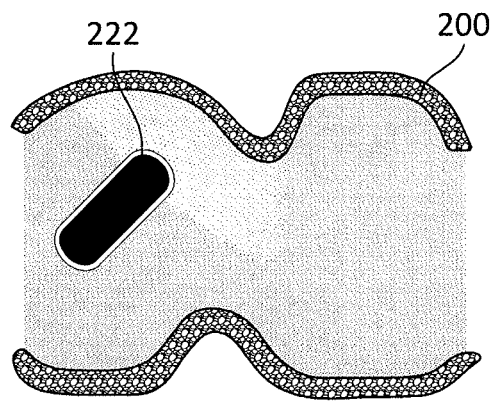
Figure 2C:
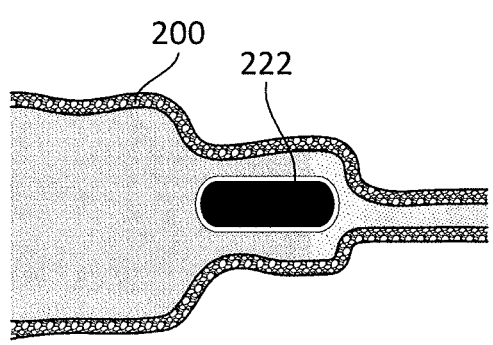
Figure 2D:
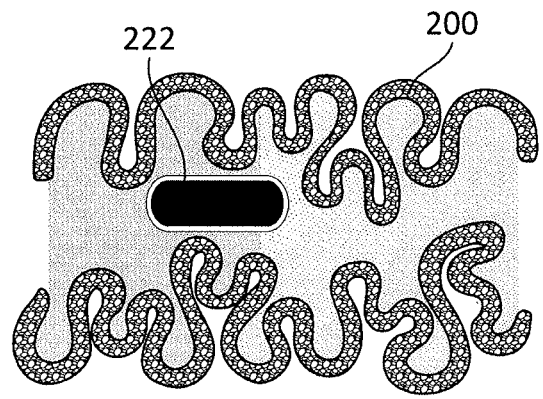
Figure 3:
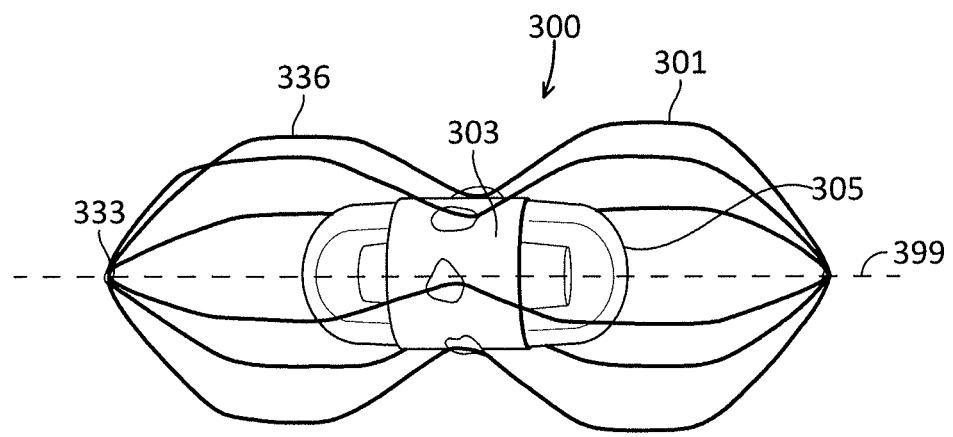
FIG. 3 shows a capsule endoscope with an exemplary luminal expansion device projecting from the proximal and distal ends.

An exemplary luminal expansion device 300 is shown in FIG. 3. The device 300 includes a central attachment mechanism 303 configured to attach to the capsule endoscope 305. For example, the attachment mechanism 303 can be an annular ring. Further, the attachment mechanism 303 can be configured to attach by friction fit, adhesive, clamp, or other attachment mechanism to or around the capsule endoscope 305. The attachment mechanism 303 can be positioned, for example, around the central portion and/or end of the capsule endoscope 305 while still maintaining a clear lens.

A plurality of radiating struts 301 extend from the attachment mechanism 303. The struts 301 emerge from the attachment mechanism 303 (and thus the capsule endoscope 305), extending both axially and radially outward from the camera lens. In other words, the struts 301 are positioned away from the end of the capsule endoscope 305 along the axis 399 (or parallel to the axis 399). The struts 301 also extend radially away from the central axis 399. The struts 301 can each form a shoulder 336 that is radially offset from the camera lens (i.e., to hold tissue away from the sides of the lens of the capsule endoscope 305). The shoulder 336 can be positioned at the maximum radial distance away from the capsule endoscope 305. Further, the shoulder 336 can be axially offset away from the body of the capsule endoscope 305. Further, the struts 301 can meet or cross at an apex 333, i.e., at a point positioned a maximum axial distance away from the lens of the capsule endoscope 305. In one embodiment, and as shown in FIG. 3, the struts 301 can form a loop made of two continuous struts. The struts 301 can form a frame (e.g., a cage, space frame, wire frame, stent cage, or tenting structure). The frame can be, for example, conical, tapered, or wedge-shaped with the apex 333 forming the tip and the struts widening out to the shoulders 336 before extending back, and then in towards the capsule endoscope 305.

In use, the struts 301 can be configured to distend tissue (e.g., within the small intestine) such that luminal folds are unfolded, enabling more complete visualization. The apex 333 can act as the leading edge while the wedge or conical shape of the tip can open tissue up as the device 300 moves through, maintaining an open field of view for the camera of the capsule endoscope 305. The shoulders 336 can help maintain a wide field of view in front of the lens. Moreover, the gaps between the struts 301 can create apertures that allow direct, unobscured tissue viewing. The primarily open structure of the device 300 can further enable the thru-passage of matter, such as chyme, during use.

Figure 4:
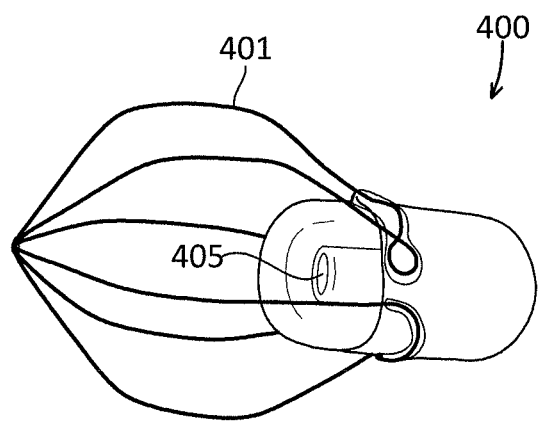
FIG. 4 shows a capsule endoscope with an exemplary luminal expansion device projecting from the distal end.

As shown in FIG. 3, in some embodiments, struts 301 can extend from both the proximal end and the distal end (e.g., so as to allow for imaging through lenses on both the proximal and distal ends). In other embodiments, as shown in FIG. 4, the device 400 can include struts 401 that extend only from a single end of the capsule endoscope 405.

Figure 5A:
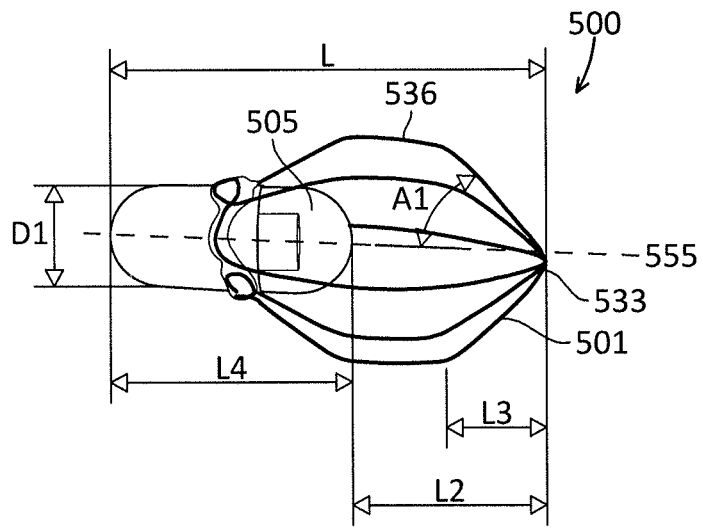
FIGS. 5A-5B show dimensions of an exemplary luminal expansion device.
Figure 5B:
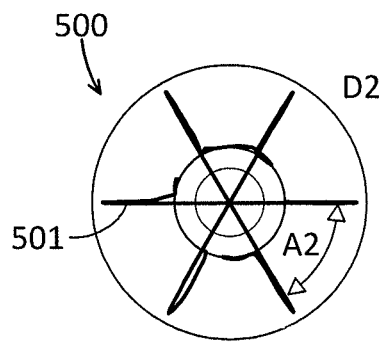

Referring to FIGS. 5A-5B, the expansion device 500 can have struts 501 with configurations and dimensions that enable efficient and effective expansion of the lumen. For example, the length L from the apex 533 to the opposite end of the capsule endoscope 505 (i.e., the length of the device 500 plus the endoscope 505 when the device 500 is positioned on the endoscope 505) can be 35 mm-80 mm, such as 50-70 mm. Further, the length L2 from the end of the scope 505 to the apex 533 (i.e., the axial length that the apex 533 extends away from the scope 505) can 10 mm-50 mm, such as 25-45 mm. The length L3 (e.g., the length of the taper from the shoulder 536 to the apex 533) can be 5 mm-40 mm, such as 10 mm-30 mm. The length L4, i.e., the length of the capsule endoscope 505, is typically 24 mm-31 mm, and the diameter D1, i.e., the diameter of the capsule endoscope 505, is typically 9-13 mm, such as approximately 11 mm. The diameter D2 of the device 500 (i.e., from shoulder 536 to shoulder 536) can be 15-65 mm, such as 20-40 mm. Further, the angle of the taper A1 (i.e., the angle that a strut 501 makes with the longitudinal axis of the device 555) can be 30° to 60°, such as 45°. Finally, the angle A2 between neighboring struts 501 can be, for example, 30 to 120 degrees.

The number of struts in each expansion device, and their contacting areas, can vary. For example, the device can include between 3 and 12 struts, such as between 4 and 6 struts, on the distal side and/or the proximal side of the capsule endoscope.

Further, the struts can be spring-like, resilient, or deformable, such that they create an expansive outward force, but are also still flexible enough such that they can be compressed by a sphincter, orifice, or stricture. In some embodiments, for example, the struts can be made of Nitinol wire and can have a diameter, for example, of 0.010 inches to 0.020 inches, such as 0.013 inches or 0.016 inches. In another embodiments, the struts can be made, for example, of a collagen or PEEK suture material and can have a diameter, for example, of 0.020 inches to 0.060 inches, such as 0.030 inches.

Figure 6:
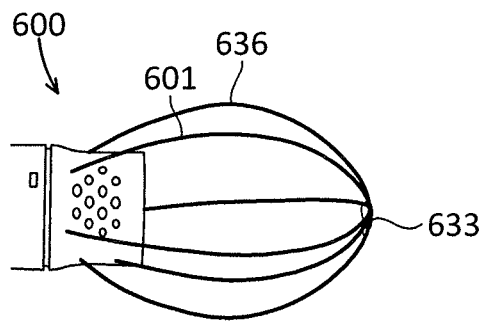
FIG. 6 shows an exemplary rounded luminal expansion device.
Figure 12:
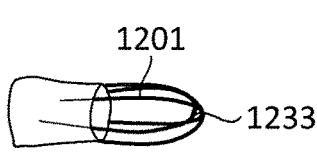
FIG. 12 shows a luminal expansion device in a rounded dome shape with a low curvature.
Figure 13:
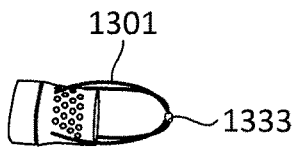
FIG. 13 shows a luminal expansion device in a rounded dome shape with a medium curvature.
Figure 14:
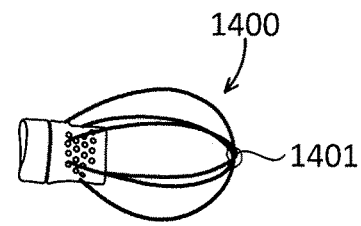
FIG. 14 shows a luminal expansion device in a rounded dome shape with a high curvature.

In some embodiments, as with devices 300, 400, 500, the shoulder area (335, 436, 536) can extend substantially parallel to the longitudinal axis of the device, thereby creating a non-rounded or flattened portion of each strut. In other embodiments, as shown in FIG. 6, the struts 601 of the device 600 can be rounded through the shoulder 636. Further, in some embodiments, the struts 601 can be rounded through the apex 633. For example, the device 600 can take on a rounded dome shape. Similar rounded dome-shaped devices are shown in FIGS. 12-14. In FIG. 12, for example, there are six struts 1201 that extended in a rounded dome shape and meet at apex 1233. FIG. 13 similarly has four struts 1301 that extend through rounded shoulders and meet at apex 1333. The struts 1201, 1301 of FIGS. 12 and 13 have a fairly low curvature and result in a frame or cage with a fairly low diameter (e.g., with a diameter that is only 10-30% greater than the diameter of the capsule itself). In contrast, FIG. 14 shows a device 1400 with struts 1401 that have larger curvature and result in a frame or cage with a fairly high diameter (e.g., with a diameter that is 50%-150% greater than the diameter of the capsule itself).

Figure 15:
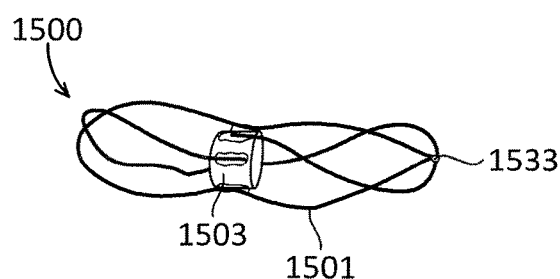
FIG. 15 shows a luminal expansion device with struts spiraled away from the attachment mechanism.
Figure 16:
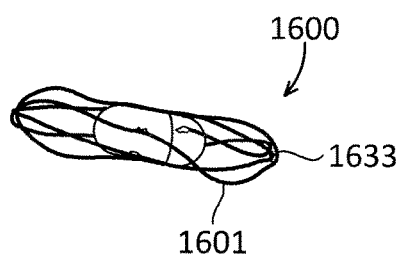
FIG. 16 shows another luminal expansion device with struts spiraled away from the attachment mechanism.

Referring to FIG. 15, in some embodiments, the struts 1501 can be spiraled away from the attachment mechanism 1503. That is, while the struts 1501 meet in an apex 1533, they do not extend in a single plane that is extends through the central longitudinal axis (as in devices 300, 400, 500, 600). Rather, each strut 1501 wraps circumferentially around the longitudinal axis of the capsule endoscope 1505 (while still extending radially outwards and axially away from the attachment mechanism 1503). FIG. 16 shows a similar device 1600 with struts 1601 that both spiral and extend through an apex 1633.

Referring to FIGS. 22A-22C, in some embodiments, the struts 2201 can be positioned such that the apex 2233 is near or adjacent to the proximal and/or distal end of the capsule endoscope 2205 while the struts are held or positioned a set radial distance away from the capsule endoscope 2205 along substantially the entire length of the scope 2205. In this configuration, the shoulder 2236 is positioned radially away from, and axially aligned with the capsule endoscope 2205. In such an example, the attachment mechanism between the capsule endoscope 2205 and the struts 2201 can be, for example, at the apex 2233. The device 2200 can be advantageous for a capsule endoscope that has side-viewing cameras (such side-viewing cameras can utilize multiple cameras configured in an array, typically each at or near the capsule endoscopes's axial center).

Figure 8:
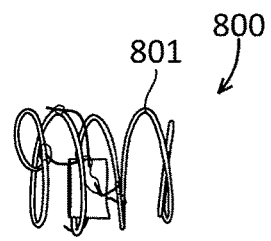
FIG. 8 shows a spiral luminal expansion device.

Further, as shown in FIG. 8, in some embodiments, the expansion device 800 can include a coiled strut 801 that coils or spirals around the attachment mechanism 803. The coiled strut 801 can be coiled so as to extend away from the attachment mechanism 803. Further, in some embodiments, as shown in FIG. 20, the coiled strut 2001 can taper down at the proximal and/or distal end to aid in navigating through the lumen.

Referring to FIGS. 17-19, in some embodiments, the expansion device can include a cage that is made of a plurality of strut elements that interconnect at various locations. For example, device 1700 includes a plurality of struts 1701 that meet at a circular ring 1717 in a cylindrical shape and then continue on to apex 1733. FIG. 1800 shows a device 1800 with struts 1801 that cross-over mid-way down the frame to form a substantially spherical shape. Finally, FIG. 19 shows a device 1900 with struts 1901 that form a disk-shaped cage.

Figure 9:
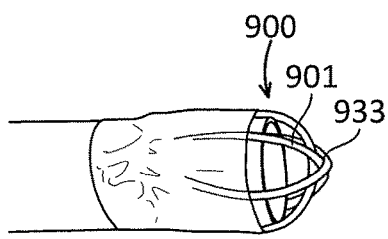
FIG. 9 shows a luminal expansion device including an injection molded dome with struts.
Figure 10:
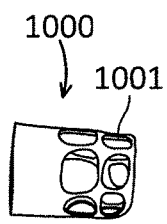
FIG. 10 shows an injection molded luminal expansion device with a plurality of apertures therein.
Figure 11:
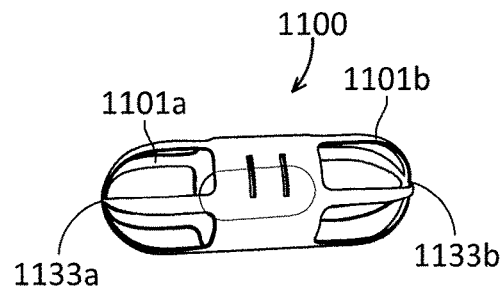
FIG. 11 shows an injection molded luminal expansion device with domes on the proximal and distal ends.

In some embodiments, the expansion device can be injection molded, such as an injection-molded polymer (e.g., PEEK, polypropylene, polyethylene, or a high durometer elastomer such as silicone or urethane). For example, FIG. 9 shows a device 900 that includes an injection molded dome that is formed of struts that meet at an apex 933. FIG. 11 shows a similar injection-molded device 1100 with domes on both the proximal and distal ends that are made of struts 1101a,b that meet at an apex 1133a,b. Further, FIG. 10 shows an injection molded device 1000 having a series of interconnected struts 1001 that form open cells around the perimeter thereof.

In some embodiments, the device can include a central strut with radiating umbrella-like tip elements.

Figure 23A:
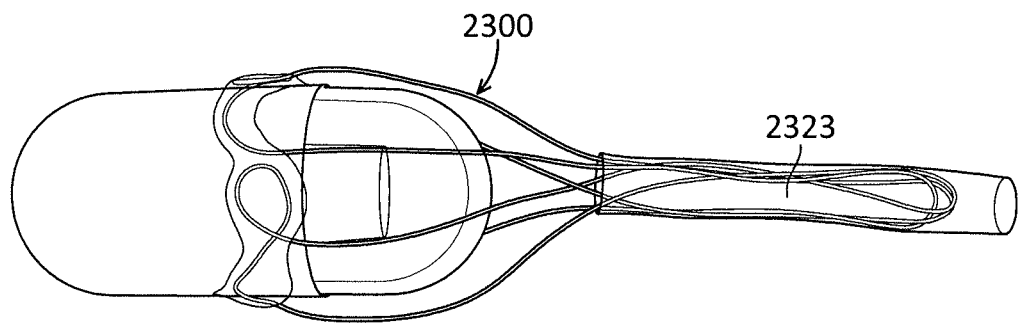
FIG. 23A shows use of a tube to collapse a luminal expansion device.
Figure 23B:
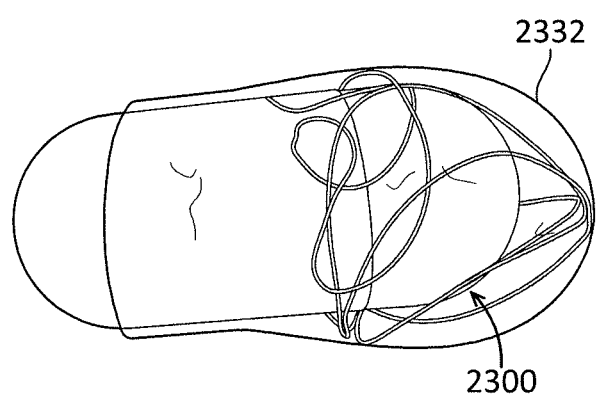
FIG. 23B shows a capsule over a collapsed luminal expansion device.

In some embodiments, the expansion device can have a geometry that enables collapsing for oral entry, as seen in FIG. 23A-B. For example, the device 2300 (which can be any of the devices described herein) can be folded, bent, rolled-up, spiral wound, or compressed to the collapsed configuration. Further, as shown in FIG. 23A, in some embodiments, a tube or constricting sheath 2323 can be used to collapse the frame. Moreover, as shown in FIG. 23B, a covering (e.g., a gel-cap covering) 2332 can be used to hold the device 2300 in the collapsed configuration. In some embodiments, the covering 2332 can be dissolved in the body, thereby allowing the device to expand into a larger configuration (e.g., the configurations otherwise shown herein).

The covering 2332 can be formed, for example, of polymers used in the pharmaceutical industry that selectively dissolve in the presence of fluids found in different anatomies, including enteric coatings for the delayed release of orally administered medications (Torpac Inc, Fairfield, N.J.). Other examples include cellulose acetate phthalate (C-A-P, Eastman Chemicals, Kingsport, Tenn.), Eudragit L 100 and S 100 (Evonik Industries, Darmstadt, Germany), Acryl-ese (Colorcon, West Point, Pa.), and Surelease (Colorcon). In some embodiments, the material for the covering 2332 can be chosen to dissolve in the colon (e.g., Eudragit S 100) or in the small intestine (e.g., other material listed hereinabove). The polymer dissolution profiles of the chosen material can be engineered from seconds to weeks, depending on the desired imaging location. Further, the covering 2332 can be single-coated, or double, triple, quadruple, or more coatings.

In some embodiments, the expansion devices described herein can have intersections (e.g. strut joints) that are fixed, pivot, hinge, slide, or are unattached in order to aid in collapse.

Once the expansion device it is in the stomach or small intestine, the struts can be expanded. For example, the struts can self-expand due to, e.g., being made of a shape memory material, such as Nitinol.

In some embodiments, expansion can occur once the device is in the small intestine. In other embodiments, expansion can occur once the device is in the stomach or the colon.

Further, expansion can occur, for example, based upon a trigger, including the chemical environment (e.g., pH since the stomach is more acidic than the small intestine), moisture, pressure, temperature, or enzymatic activity, time, location, or visual clues (e.g., the camera can recognize villi, which only occur in the small intestine). In other embodiments, expansion can occur, for example, based upon a dissolution mechanism (such as dissolution of the covering described above) or micro-actuators that are electrically triggered (including the use of micro motors, reed switches, magnetic actuators, piezo actuators, nitinol heated by a battery, or a membrane heated by a battery to release gas, chemicals, or mechanical motion).

Referring to FIGS. 24-26B, in some embodiments, elements of the frame and/or struts can be biodegradable and/or can include biodegradable (bio-decaying or corroding) nodes. The nodes can be placed at the joints (i.e., at the junction between two struts) or can be placed within a strut. The biodegradable elements or nodes can detach, shrink, disintegrate, or dissolve before the device is expelled by the body. When dissolved, the struts and/or strut sub-elements (if the nodes are within the strut) can separate from one another to help with expulsion. Such biodegradable materials can include: Magnesium alloys, absorbable suture materials (including PGA, PLA, PLGA and collagen), PVA plastics (including Aquasol and Monosol), lactose, cellulose-acetate, and a range of bio-based plant materials, including cotton, flax, bamboo, jute, hemp, wood, coconut. In some embodiments, the biodegradable elements can be made of edible material, for example pasta derivatives.

Figures 24, 25A:
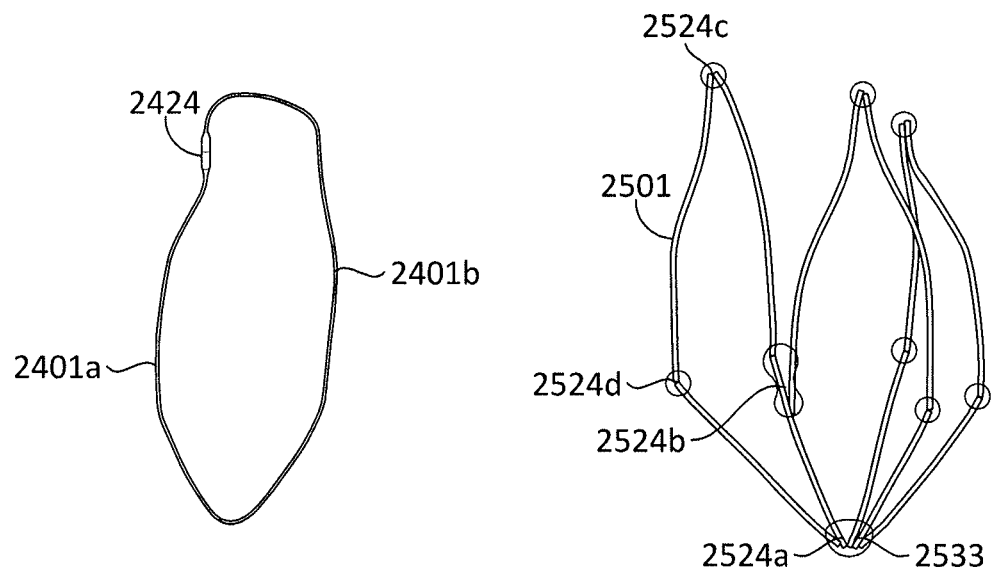
FIG. 24 shows a loop of a luminal expansion device.
FIG. 25A shows a luminal expansion device with biodegradable nodes.
Figures 25B, 26A, 26B:
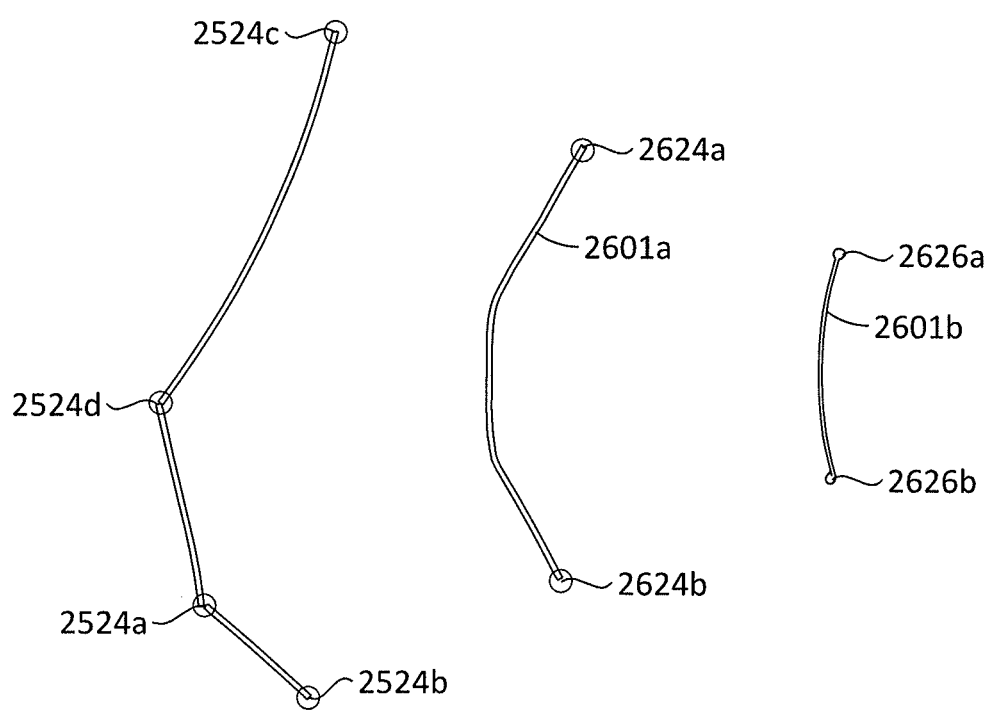
FIG. 25B shows a separated portion of the luminal expansion device of FIG. 25A.
FIGS. 26A-26B shows struts that have been dissolved from a luminal expansion device.

As shown in FIG. 24, a device 2400 can include two struts 2401a,b connected together in a loop by node 2424. In some embodiments, the node 2424 can be biodegradable to allow the loop to separate into a straight segment. In other embodiments, the node 2424 can be permanent such that the loop itself can pass (e.g., the loop can be configured to biodegrade from a larger frame structure). As shown in FIG. 25, a device 2500 can include six struts 2501 and a plurality of biodegradable nodes 2524. For example, nodes 2524a, 22524b, and 2524c can all partially or fully dissolve to create an elongate piece that more easily passes, as shown in FIG. 25B. FIGS. 26A and 26B show additional struts 2601a,b and nodes 2624a,b that would be the resultant elements after nodal decay.

As shown in FIGS. 25-26B, each node can encase a joint between two struts or strut segments. Further, the nodes can be spherical or ovoid. In addition, as shown in FIG. 26B, the ends 2626a,b of each strut 2601 at the node can be spherical or otherwise atraumatic so that they do not harm the tissue upon dissolution of the nodes.

In some embodiments, the struts can be pre-shaped such that they coil or otherwise shrink into smaller shapes once they have been separated at biodegradable joints.

Figure 27:
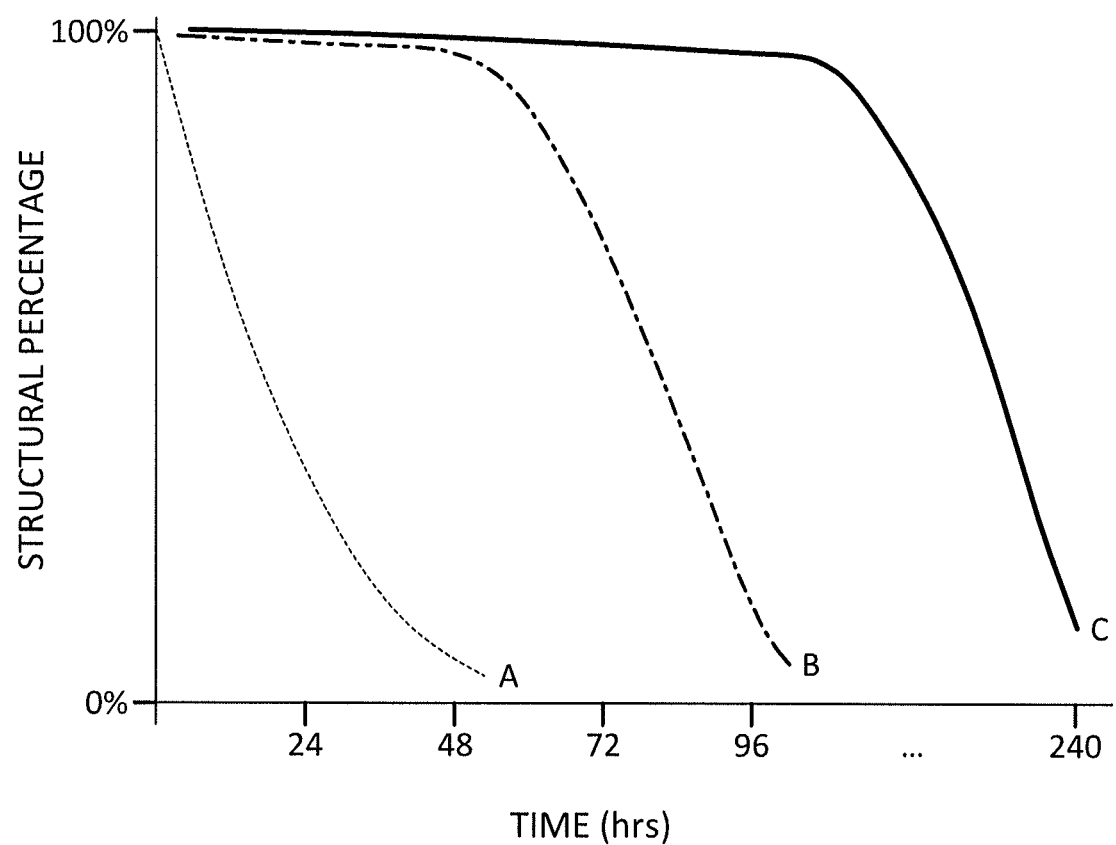
FIG. 27 shows exemplary decay rates of different nodes of a luminal expansion device.

In some embodiments, the expansion device can have components with different dissolution rates. In one example, there can be sub-element struts that decompose slowly (e.g. over days or weeks) coupled by fusible nodes that decompose more rapidly (e.g., within 24 hours). An exemplary chart of dissolution of structures is shown in FIG. 27, where curve A signifies a faster decay time, and curve C signifies a slower decay time.

In some embodiments, the entire structure of the struts can decompose.

Dissolution of all or portions of the devices described herein can aid in passage through the body.

In some embodiments, the struts or other surfaces of the devices described herein can have surface features incorporated thereon. For example, the struts can have coatings that create either enhanced or lowered frictional values. The surface features in some embodiments can be very small external protrusions or scales to create a retarding or grabbing effect.

The expansion devices described herein can be comprised of a material that does not readily corrode. The material can be elastic or superelastic (e.g., nitinol). The material can be, for example, a hydrocarbon or a plastic, such as nylon, polycarbonate, or polyethylene, or an elastomer, including a silicone, urethane, or pebax. The struts and other structures of the devices described herein can be heat set, molded, cast, adhered, or otherwise formed.

In some embodiments, the devices described herein can be covered with one or more sheets, including clear sheets. The sheets can be treated so that they readily repel or attract wet tissue.

In some embodiments, parts of the expansion devices described herein can be infused with radio-opaque materials to aid in fluoroscopy visualization.

In some embodiments, the luminal expansion devices described herein can be symmetrical (i.e., can be created through an axis of rotation). In other embodiments, the devices can be asymmetric.

In some embodiments, the leading edge or apex of the expansion device can be tapered, bullet-nosed, conical, or rounded.

The struts of the devices described herein can have a circular, oval, square, rectangular, or other cross section.

The struts of the devices described herein can be monolithic, i.e., made of a single material. In other embodiments, the struts can be composite structures, such as be made of tubes with an outer layer (with its own properties and materials) and an inner portion (with its own properties and materials). In one embodiment, the struts can be small tubes that are inflated with a pressurized fluid or gas.

Figure 7:
FIG. 7 shows a luminal expansion device including an inflatable element.

In some embodiments, referring to FIG. 7, the devices described herein can include an inflatable element 777, such as a balloon, configured hold the tissue away from the capsule. The inflatable element 777 can be used in addition to or in place of the cage and strut elements described herein.

The expansion devices described herein can attach to the housing of the capsule endoscope or to the optical hood of the capsule endoscope. In some embodiments, the expansion device can be designed as an integral part of the capsule endoscope.

Figure 28:
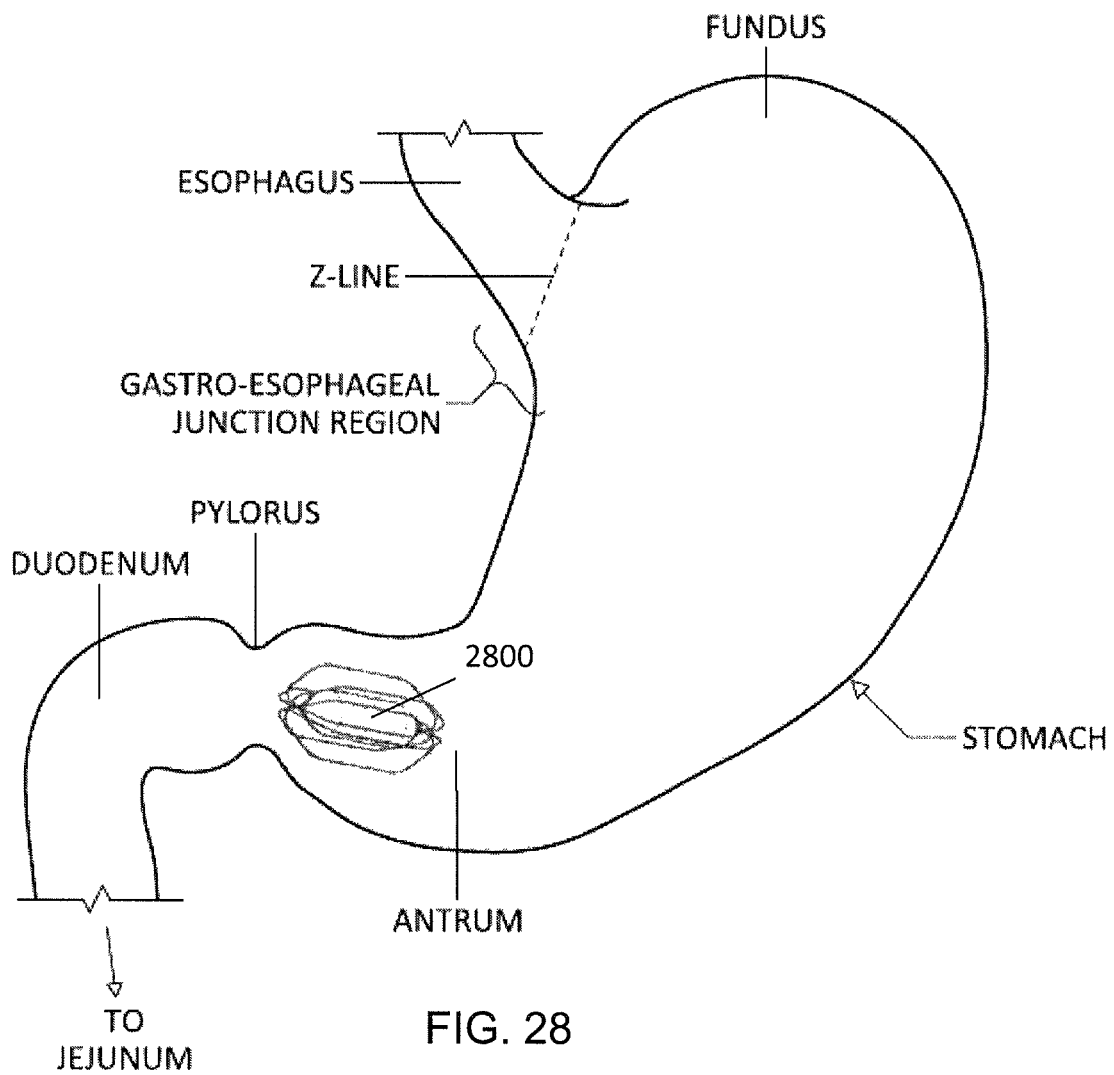
FIG. 28 shows use of a luminal expansion device inside the gastrointestinal tract.

Referring to FIG. 28, an expansion device 2800 as described herein can advance like other swallowed capsule endoscope devices, i.e., thru GI-tract contractions, including peristalsis. The device may not retard speed-of-passage, but instead it can enhance speed-of-passage, in effect serving to 'super-trigger' peristalsis, including through enhanced area, length, and contact points. The device can thus be used to image, for example, the small intestine or the colon.

Figure 29:
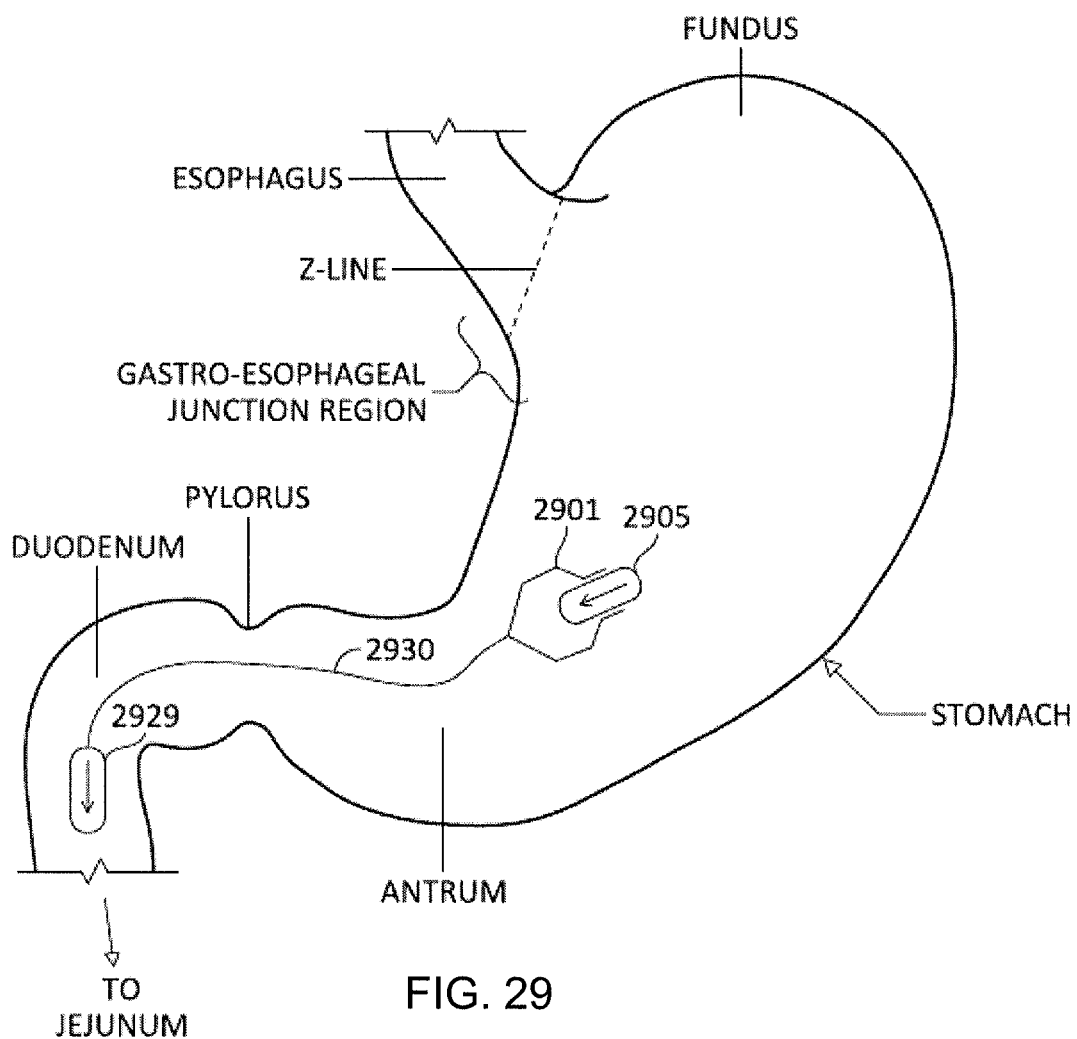
FIG. 29 shows a luminal expansion device with a tug used inside of the gastrointestinal tract.

Further, referring to FIG. 29, in some embodiments, a small tug element 2929 can be attached to the struts 2901 with a tensile member 2930. The small tug element 2929 can thus easily pass through the pylorus and, as it is propelled, pull the struts 2901 and attached capsule endoscope 2905 through the pylorus and into the duodenum.

Alternatively, in some embodiments, the expansion device (and capsule endoscope) can be directly placed into the stomach with an ancillary device.

Figure 30A:
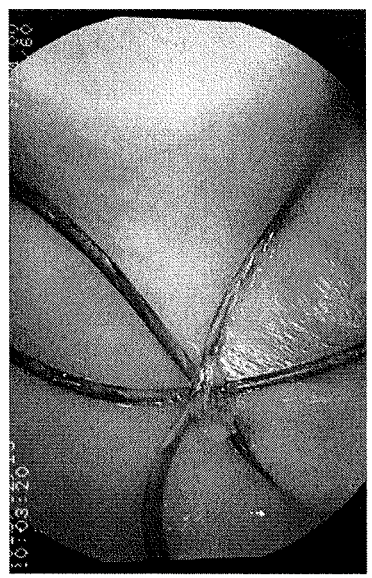
FIG. 30A shows an image gathered from a capsule endoscope inside a lumen when a luminal expansion device is used.
Figure 30B:
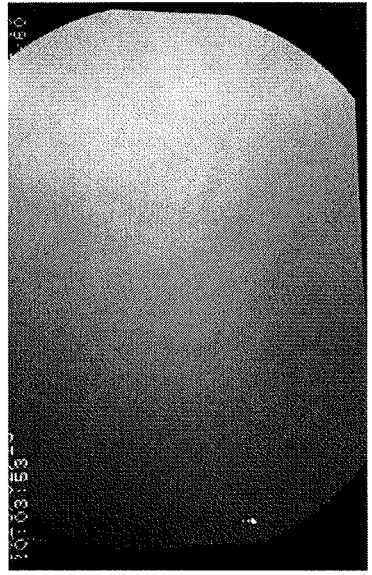
FIG. 30B shows an image gathered from a capsule endoscope inside a lumen when a luminal expansion device is not used.

The expansion devices described herein can advantageously improve the field of view when used with a capsule endoscope. FIG. 30A shows an image gathered of a small intestine with a capsule endoscope when an expansion device is used while FIG. 30B shows the image gathered without. As shown in FIG. 30B, tissue covers the lens when the expansion device is not used, thereby making it difficult to visualize within the small intestine. In contrast, when the expansion device is used (FIG. 30A), the expansion device holds the tissue away from the camera, allowing better visualization of the lumen. Because both the length and the diameter of the expansion devices described herein are larger that of the capsule endoscope itself, the devices can help keep tissue away from the capsule endoscope and create better alignment with the central axis of the lumen, thereby creating a passage that is more lumen-centric and improving image quality.

Figure 21:
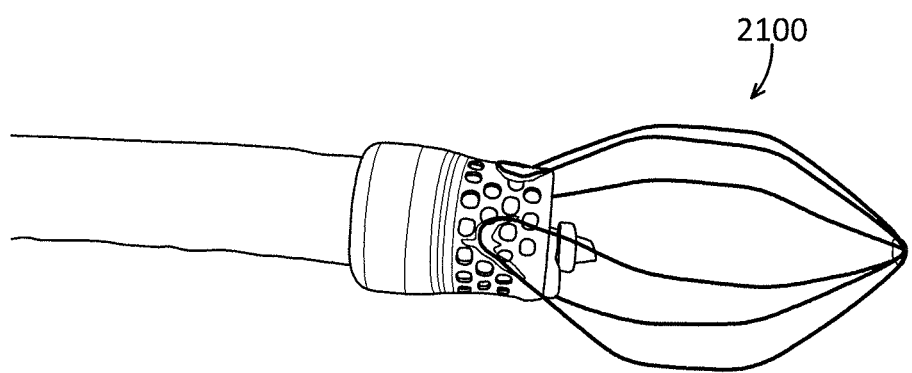
FIG. 21 shows a luminal expansion device attached to the end of a catheter endoscope.

As shown in FIG. 21, in some embodiments, rather than attaching to a capsule endoscope, the expansion device 2100 can be attached to the tip of an endoscope, such as a colonoscope. The expansion device 2100 can have similar elements (e.g., struts) to any of the expansion devices described elsewhere herein.

Any of the features or elements of any of the expansion devices described herein may be combined or substituted for features or elements of any other expansion device.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below can be termed a second feature/element, and similarly, a second feature/element discussed below can be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

What is claimed is:

1. A device for distending a body lumen for enhanced visualization with a capsule endoscope that includes a camera lens, the device comprising:
    an attachment element configured to attach to the capsule endoscope; and
    a plurality of struts extending from the attachment element and meeting at an apex, wherein the plurality of struts are configured to extend both axially and radially away from the camera lens so as to form a frame therearound with the apex positioned a set axial distance away from the camera lens.

2. The device of claim 1, wherein the attachment element is an annular ring.

3. The device of claim 1, wherein the frame includes a shoulder that comprises a portion of the frame that is positioned a maximum radial distance away from the capsule scope.

4. The device of claim 3, wherein the shoulder is axially offset away from the camera lens.

5. The device of claim 1, wherein there are between 4 and 6 struts in the plurality of struts.

6. The device of claim 1, wherein each of the plurality of struts is self-expandable.

7. The device of claim 6, wherein each of the plurality of struts is formed of a shape memory material.

8. The device of claim 1, wherein the frame includes a biodegradable portion.

9. A device for visualization of a body lumen, comprising:
    a capsule endoscope including a camera lens;
    a plurality of struts extending from the capsule endoscope and meeting at an apex, wherein the plurality of struts extend both axially and radially away from the camera lens so as to form a frame therearound with the apex positioned a set axial distance away from the camera lens.

10. The device of claim 9, wherein the frame includes a shoulder that comprises a portion of the frame that is positioned a maximum radial distance away from the capsule endoscope.

11. The device of claim 9, wherein there are between 4 and 6 struts in the plurality of struts.

12. The device of claim 9, wherein each of the plurality of struts is self-expandable.

13. The device of claim 12, wherein each of the plurality of struts is formed of a shape memory material.

14. The device of claim 9, wherein the frame includes a biodegradable portion.

15. A method of enhancing visualization of a body lumen, the method comprising:
    positioning a device including a capsule endoscope and a plurality of struts attached thereto into a body lumen;
    expanding the plurality of struts of the device within the body lumen such that the plurality of struts extend both radially and axially away from a camera lens of the capsule endoscope and meet at an apex that is positioned a set axial distance away from the camera lens; and
    imaging with the camera lens into the body lumen.

16. The method of claim 15, wherein the plurality of struts form a frame around the camera lens upon expansion, the frame including a shoulder that comprises a portion of the frame that is positioned a maximum radial distance away from the capsule endoscope.

17. The method of claim 15, wherein the plurality of struts form a frame around the camera lens upon expansion, the frame including a tapered tip.

18. The method of claim 15, wherein there are between 4 and 6 struts in the plurality of struts.

19. The method of claim 15, wherein expanding the plurality of struts comprises self-expanding the plurality of struts.

20. The method of claim 15, wherein the plurality of struts form a frame around the camera lens upon expansion, and wherein the method further comprises dissolving at least a portion of the frame to allow passage of the device from the body.

* * * * *